United States Patent [19]

Brånemark

[11] Patent Number: 5,562,670
[45] Date of Patent: Oct. 8, 1996

[54] HOLDING MEANS AND METHOD OF IMPLANTATION THEREOF IN OSSEOUS TISSUE

[75] Inventor: Per-Ingvar Brånemark, Molndal, Sweden

[73] Assignee: Medevelop AB, Sweden

[21] Appl. No.: 233,313

[22] Filed: Apr. 26, 1994

[30] Foreign Application Priority Data

Apr. 27, 1993 [SE] Sweden .................................. 93 01406

[51] Int. Cl.⁶ .................................................. A61C 8/00
[52] U.S. Cl. ............................................. 606/73; 607/116
[58] Field of Search ................................. 606/72, 73, 65; 607/116, 136, 137

[56] References Cited

U.S. PATENT DOCUMENTS

| | | |
|---|---|---|
| 3,870,832 | 3/1975 | Fredrickson . |
| 4,606,329 | 8/1986 | Hough . |
| 5,057,108 | 10/1991 | Shetty et al. . |
| 5,064,425 | 11/1991 | Branemark et al. ............... 606/72 |
| 5,209,753 | 5/1993 | Biedermann et al. ............... 606/73 |

FOREIGN PATENT DOCUMENTS

| | | |
|---|---|---|
| 3141459 | 10/1991 | Germany . |
| 8604973 | 2/1990 | Sweden . |
| 8302047 | 6/1983 | WIPO . |
| 9118556 | 12/1991 | WIPO . |

OTHER PUBLICATIONS

Journal of Biomedical Engineering, vol. 5, No. 1, Jan. 1983–Direct Bone Anchorage of External Hearing Aids—A. Tjellstrom, J. Lindstrom, O. Hallen, T. Albrektsson and P–I Branemark.

*Primary Examiner*—William E. Kamm
*Assistant Examiner*—Scott M. Getzow
*Attorney, Agent, or Firm*—Ostrolenk, Faber, Gerb & Soffen, LLP

[57] ABSTRACT

A device for implanting in osseous tissue, for example in the skull of a patient, for electric transmission of signals to the inner ear, includes a rotationally symmetric body (1) of titanium or other tissue compatible material with an insertion end (2) for insertion into a bore prepared in osseous tissue beforehand and an application end (3) intended to remain external to the patient. A central through bore (4) connects both ends (2,3) of the body. An external screw thread (7) is provided adjacent the insertion end. An insulating element (9) is arranged in the bore and carries one or more terminal elements or contacts (12) connected with insulating electrical conductors (8). The conductors (8) extend from the contacts (12) through the axial bore at the insertion end or through openings in the peripheral wall surface of the body (1). In implantation of the holding means a bore is prepared in osseous tissue, the holding means is screwed into the bore, the conductors (8) being extended through the central bore and connected to their respective contacts in the insulating element and the insulating element is secured within the central bore through the application end.

16 Claims, 2 Drawing Sheets

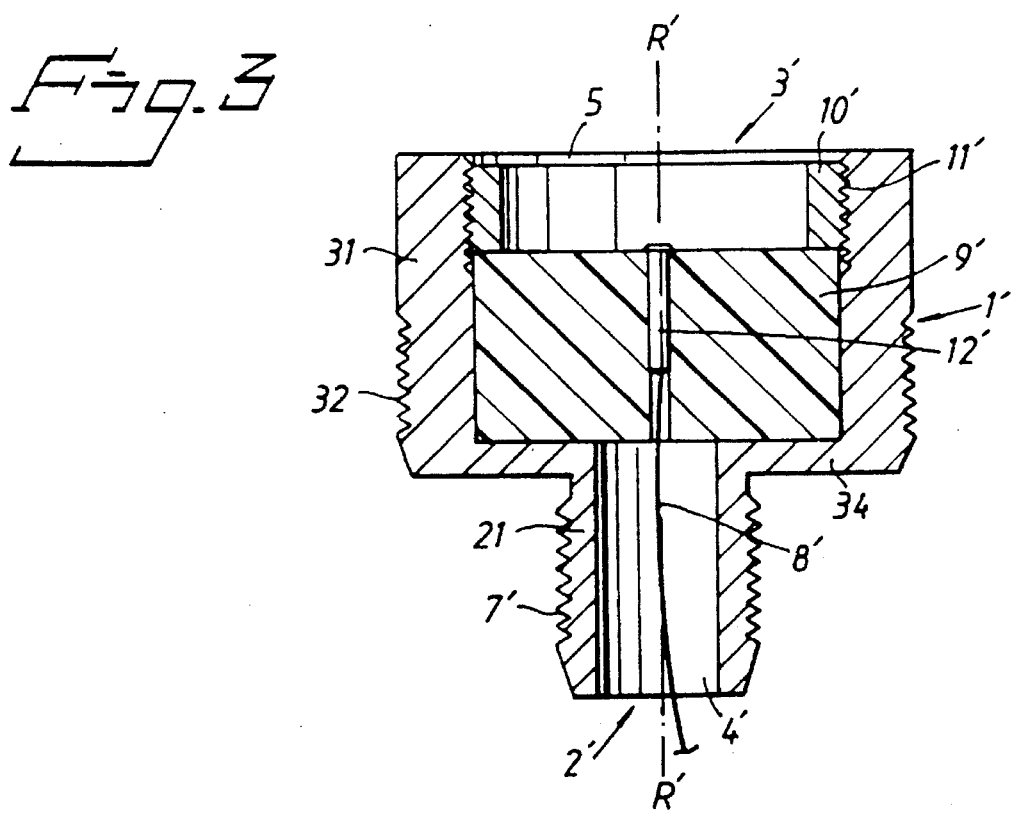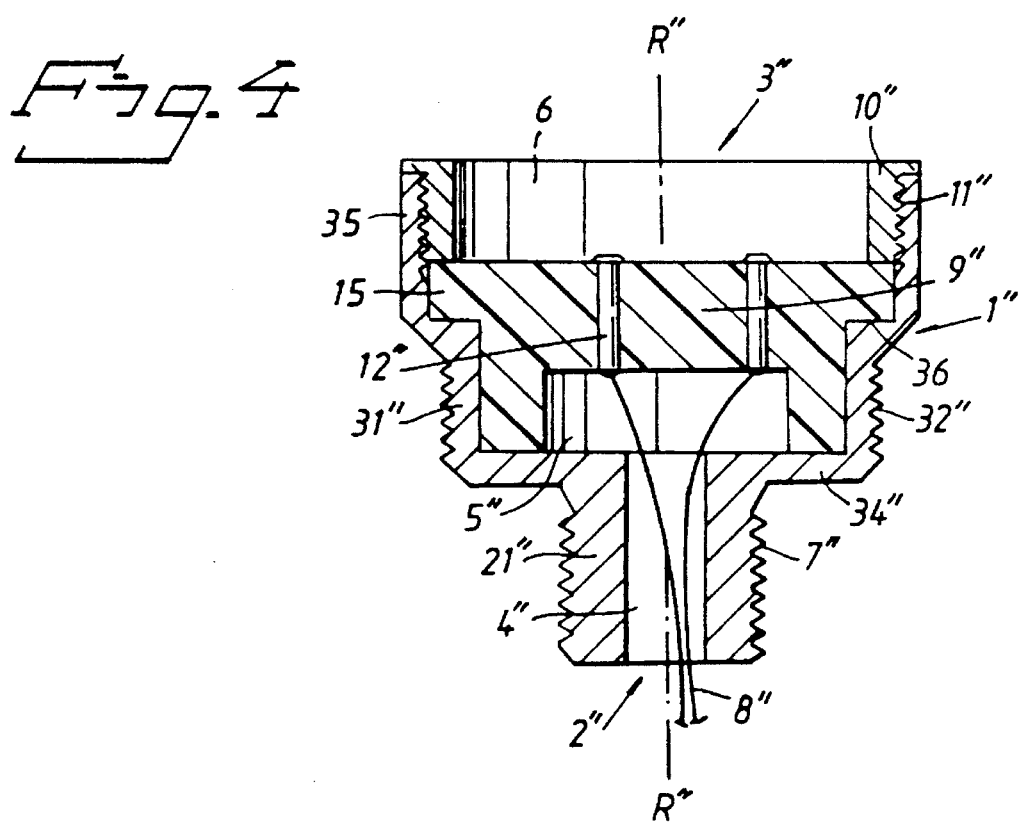

HOLDING MEANS AND METHOD OF IMPLANTATION THEREOF IN OSSEOUS TISSUE

The present invention relates to a device for implantation in osseous tissue, for example for controlled holding and fixation of equipment for electrical transmission of information, the device including rotationally symmetric holding means consisting of a tissue compatible material, the holding means being provided with external threads extending from its one end (insertion end) towards its opposite end (application end). The invention also relates to a method of implanting such a device in osseous tissue.

Rotationally symmetric anchoring means provided with external threads and intended for implantation in osseous tissue are known and described in, for instance, U.S. Pat. No. 5,064,425. Such anchoring means have been used with great success for holding artificial teeth, tooth bridges and also for holding prostheses, artificial joints in connection with reconstruction of joints, etc. In respect of dental applications, such anchoring means are marketed by NobelPharma AB, Sweden under the trademark Brinemark System®.

For a long time there has been a need for a device affording a communication through the skin for electrical conductors, for example, and capable of supporting an electrical connector, for example. Such a device would be of utility for example for transferring information to the inner ear in persons with impaired hearing.

An object of the present invention is to provide such a device which, on the one hand, can be positionally fixed in a controlled way by anchoring in bone tissue and, on the other hand, is able to receive electrical or other connections necessary for that purpose.

In accordance with the invention, there is provided a device for implantation in osseous tissue including rotationally symmetric holding means consisting of a tissue compatible material, the holding means having an insertion end and an application end and being provided with an external thread or threads extending from said insertion end thereof towards said application end, said holding means having at least one axial bore extending from the application end of the holding means to the insertion end of the holding means.

In one embodiment of the invention the application end of the holding means is arranged for receiving contact elements and a connector device for cooperation with said contact elements.

Preferably the holding means has an inner bore provided with various inner diameters, the portion of the inner bore with the largest diameter being positioned adjacent to the application end of the bore.

At its application end the device is preferably provided with locking means for fixing a connector element or plug in position.

The connector element or plug may be provided with male or female contacts for electrically conductive connection of conductors to electrical circuitry arranged exteriorly of the holding means, such as signal-producing, signal-receiving and current-supplying circuitry.

Preferably the insertion end of the holding means is provided with slits extending from the insertion end of the holding means towards the application end, and intersecting the screw threads, the edges of said slits forming cutting edges whereby the holding means is self-tapping, i.e. will form a complementary screw thread in a bore in bone tissue into which it is screwed.

In one embodiment of the invention the holding means comprises a first holding portion with first external threads and a first central bore as well as a second holding portion axially attached to the first holding portion with which it is integrally formed and having a second central bore, said first and second holding portions and the central bore being co-axial with the remainder of the holding means and the first holding portion being insertable with its free end into a bore prepared in bone tissue beforehand, and the outer diameter of the second holding portion being at least as large as the outer diameter of the first holding portion, the diameter of the second central bore being larger than the diameter of the first central bore and the second central bore being designed for holding an electrically insulating body supporting an electrical contact or contacts, the first central bore receiving a conductor or conductors extending from the contact or contacts.

At least in its portions having contact with tissue after implantation the holding means is preferably of titanium and has, at least on the portion of its surface having tissue contact after implantation, a micropitted surface with a pit diameter of between 10–1,000 nm, preferably between 10 and 300 nm. Thereby optimal conditions are provided for good anchoring between the cell extensions of bone tissue and said micropits.

The invention also comprises a method for the implantation in osseous tissue of a holding means such as described above; the method comprising:

providing a hole in osseous tissue, the diameter of the hole substantially corresponding to the root diameter of the externally threaded portions of the holding means, inserting the holding means into the hole by screwing, inserting at least one conductor for electrical signals into the central bore, said conductor being provided with an extension exteriorly and interiorly of a portion bordering the insertion end of the holding means, and securing an electrical contact device coupled to the conductor at the application end of the holding means.

In a variant embodiment the electrical conductor or conductors can also be diverted from the inner bore via openings provided in the peripheral wall of the holding means.

Embodiments of the invention are described below by way of example with reference to the accompanying drawings.

IN THE DRAWINGS

FIG. 3 shows another embodiment of the invention, again in longitudinal section through the axis R' of rotational symmetry; and FIG. 4 shows a yet further embodiment in longitudinal section through the axis R" of rotational symmetry.

Figure 1:
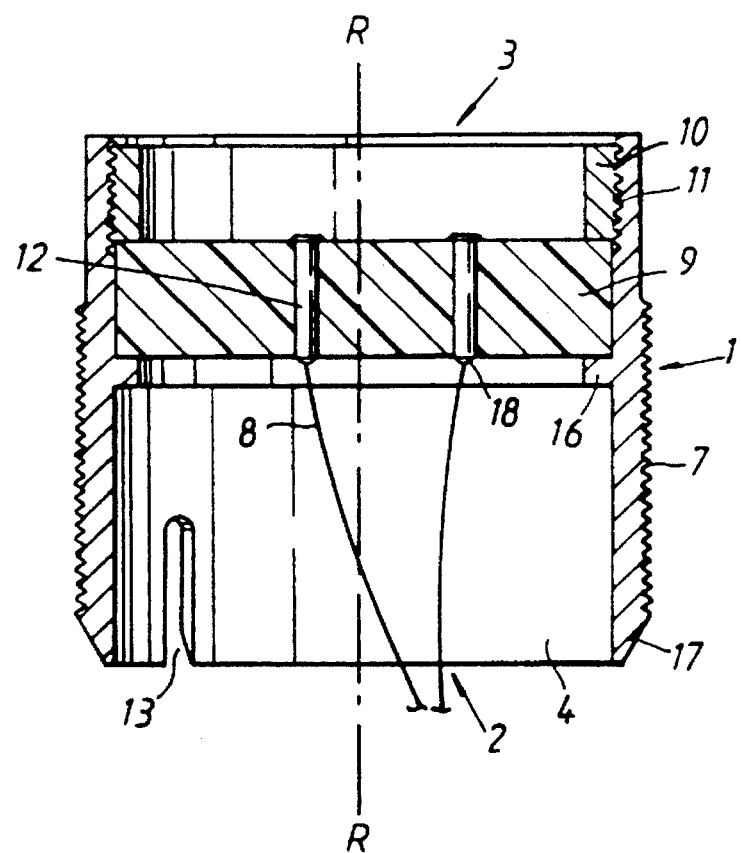
FIG. 1 is a view of a device constituting a first embodiment of the invention, in longitudinal section through the axis R of rotational symmetry of the holding means.

The holding means shown in FIG. 1 comprises a body 1 in the form of a hollow cylinder of titanium having an axial bore 4 extending therethrough, with bore 4 being bounded by a cylindrical peripheral wall of body 1. The holding means has an external thread 7 extending from its one end 2 in the direction of the other end 3. In a section adjacent to the application end 3 the peripheral surface of the body 1 is plain and smooth.

The end 2 is herein referred to as the insertion end and is the end which is inserted first into a hole prepared in bone tissue in implantation of the device, for example into a hole prepared in the skull of a patient. The opposite end of the holding means, herein referred to as the application end, projects through the patients skin after the device has been implanted.

An internal annular rib or flange 16 which projects from the inner bore 4 towards the central axis is located about halfway between the ends 2,3. The surface of flange 16 facing towards the application end 3 is abutted by a polypropylene insulating element 9 of cylindrical form, which fits closely with the bore 4. A portion of the bore 4 adjacent to the application end 3 is provided with a screw thread 11 and receives a locking ring 10 provided with a corresponding external thread. The ring 10 is screwed into the threaded part of bore 4 until it engages the end face of element 9 remote from flange 16, thereby clamping the element 9 in position.

Figure 2:
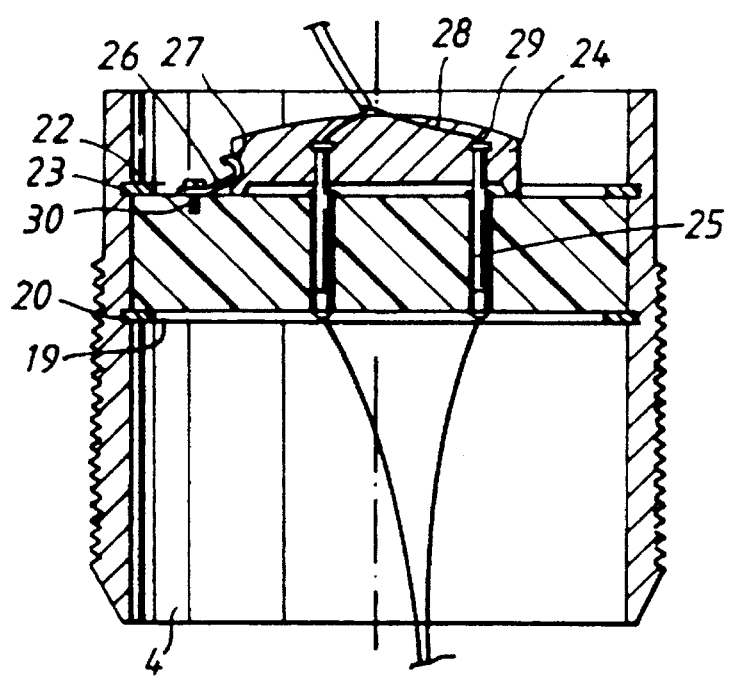
FIG. 2 shows a variant of the device of FIG. 1, with an electrical connector coupled thereto.

At the insertion end 2 three longitudinal slits or incisions 13 directed towards the application end 3 are arranged in the cylindrical wall of body 1; only one such slit 13 is shown in FIG. 2. The edges of these slits provide cutting edges which make the body self-tapping when the holding means 1 is screwed into a bore prepared in osseous tissue beforehand.

Over a wall portion 17 extending from the insertion end 2 the wall thickness of the body 1 tapers towards the insertion end 2, (i.e. the end 2 is chamfered). This chamfer at the end 2 facilitates the placement of the insertion end 2 of the holding element against or, rather, into the bore provided in the bone and facilitates the start of the thread cutting action of the self-tapping body.

The contact element 9 is provided with two transversely spaced tubular female contacts or sockets 12 which are made of electrically conducting material. The sockets 12 extend parallel with the contact axis of body 1 and pass completely through the element 9. To the end of each contact or socket 12 which lies nearer the insertion end 2 is soldered a respective thin flexible electrical conductor 8, e.g. comprising a copper alloy. The conductors 8 are insulated. The conductors 8 exit from the bore 4 at the insertion end 2. In a variant not shown in the drawings, one or more lateral openings are arranged in the wall of the body 1 and the conductors 8 pass through these lateral openings. The female contacts or sockets 12 can receive complementary male contacts or plugs of a connector which can be inserted into the body 1 from the outer end 3, in substantially the same way as illustrated in FIG. 2 for a variant, to be described.

In the variant shown in FIG. 2 the annular internal rib 16 has been replaced by a resilient internal locking ring or circlip received in a groove 20 milled into the inner wall of bore 4. In a corresponding manner the locking ring 10 with peripheral thread 11 is replaced by a further resilient locking ring or circlip 22 received in a groove 23 formed around the central bore. The insulating element 9 is thus located between the locking rings 19 and 22. In FIG. 2 is also shown a releasable electrical connector 24 with prongs fitting the sockets in the element 9. The connector 24 has a body of insulating material supporting prongs 25 fitting the sockets 24 and soldered at 29 to insulated conductors 28. The connector 24 is fixed to a leaf spring 26 secured to the element 9 by a screw 30. The leaf spring 26 engages in a recess 27 on the side wall of the connector 24. The variant according to FIG. 2 permits the inner bore 4 to be formed in a single manufacturing step but, on the other hand, requires milling of the grooves 20 and 23. This variant is advantageous in permitting a body 1 of given form to be adapted for receiving coupling elements of varying thickness and in providing for greater flexibility in respect of location of element 9 in bore 4.

The embodiment shown in FIG. 3 comprises a body 1' of titanium which has two co-axial hollow cylindrical wall portions 31 and 21 of respectively larger and smaller diameter connected by an annular wall portion 34. The wall portions 21 and 31 are also referred to herein as first and second holding portions 21,31 respectively. The wall portion 34 provides an annular step or abutment at the inner end of the bore in the larger diameter portion 31. The axial bore through body 1 thus has two sections, a first central bore 4' in the first portion 21 and a second central bore 5 in the second portion 31. The portion 21 forms an anchoring element and terminates in the insertion end of body 1'. The portion 21 is externally screw-threaded and is chamfered or tapered at its free end, i.e. the insertion end, referenced 2' in FIG. 3. The second section 5 of the axial bore, provides in the second wall portion, terminates in the application end, referenced 3'. The outer diameter of the first holding portion 21 is substantially smaller than the diameter of the bore 5 of the second holding portion 31. An insulating element 9' of cylindrical form and made of insulating polymer material rests on the base wall section 34 of the second holding portion 31. The portion of the bore 5 adjacent the free end is screw-threaded at 11' and, as in the embodiment of FIG. 1 receives an externally threaded anchoring ring 10'. the element 9' being clamped between ring 10' and wall 34. The connector 9 in FIG. 3 has a single central female contact or socket with an insulated conductor 8'. Not shown in FIG. 3 is the complementary connector having a male contact or prong for engagement with the female contact 12'. Both the first and the second holding portions 21,31 have external threads 7', 32 of the same pitch but, of course, of different diameters. However, external threads 32 on portion 31 extend only over approximately half of the outer wall of the second holding portion, the outer wall adjacent to the external end 3' is plain and smooth.

A further embodiment of the invention is shown in FIG. 4. In this embodiment the body of the holding means is of a form similar to that of FIG. 3 in that it has a first holding portion, referenced 21", a second holding portion, referenced 31", a transverse wall or base portion 34" connecting wall portion 21" with wall portion 31", an inner through bore with a first portion 4" in the first holding portion and a second portion 5" in the second holding portion 31" the first holding portion 21" terminating in a free insertion end 2" and first and second external threads 7", 32" being provided on portions 21" and 31" respectively. The relationship of these parts in respect of each other is the same as for corresponding parts of the embodiment shown in FIG. 3. At its end remote from the first holding portion 21", the portion 31" meets with a further hollow cylindrical portion 35 which is of greater diameter again than the portion 31" and extends co-axially with parts 21", 31" in the direction away from portion 21". The internal diameter of the portion 35 is greater the outer and inner diameters of the second holding portion 31". The connection between portion 35 and the second holding portion 31" forms an annular step or shoulder on which a flange 15 of a modified insulating element 9" rests. An annular locking ring 10" of the same form as rings 10 and 10' in FIGS. 1 and 3 respectively is screwed into a screw-threaded part 11" of the bore in the portion 35 adjacent application end 3" and secures the radial flange section 15 of the element 9" against shoulder 36. The flange 15 has a good fit within the portions 35. Except for said flange section 15 and a central recess in the side of the insulating element 9'' facing the insertion end 2'' the insulating element 9'' is of the same form as element 9 in FIGS. 1 to 2 and is similarly provided with contact sockets, referenced 12'', connected with insulated conductors referenced 8''.

The embodiments shown in FIGS. 3 and 4 can, of course, be provided with slits 13 having straight or spiral form, bevelled insertion sections, locking rings, etc., in a way similar to that described for the embodiments shown in FIGS. 1 and 2.

On implantation by surgery of the holding means shown in FIGS. 1 and 2 in, for example, the skull of a patient, the bone is surgically exposed and a bore is cut in the bone to a depth corresponding to the intended depth of insertion and having a diameter corresponding, substantially, to the root diameter of external threads 7. Depending on whether the holding means is intended to penetrate the bone or not it may be necessary to extend the bore in the bone until it penetrates the bone or to arrange in the bottom of the first-mentioned bore in the bone, a further bore of smaller diameter for a connector. This extension of the bore and the application of the conductors 8 can be executed before or after the screwing insertion of the holding means into said bone. If the conductors 8 are inserted after insertion of the holding means and via the free end 3 of the holding means the conductors 8 can already be firmly attached to the contact elements 9, for instance soldered. The insulating element 9 need only be inserted into the bore 4 via the free end 3 of body 1 and secured in the bore by means of the locking ring 10 or the circlip 23. The depth of insertion is selected to provide for the thread-free area of the holding mantle to extend exteriorly of the periosteum. In certain areas the peripheral surface of body 1 can be given a particular form and/or provided with a surface treatment to ensure skin penetration of good quality (if there is skin penetration), such as with a cochlear prosthesis.

The holding means shown in FIGS. 3 and 4 are implanted by surgery in a similar way except for two coaxial bores being made in the bone, the first one being of larger diameter corresponding to the root diameter of the external threads 32,32'', and the second being of smaller diameter corresponding to the root diameter of the external threads 7',7'' and with a minimum depth corresponding to the axial length of the first holding portion 21,21''.

The holding means according to the invention can be advantageously used for transmission of information to the inner ear but also for other purposes. In or adjacent to the holder, microchips, batteries or other electric equipment can also be accommodated The element 9,9',9'' can also be provided with a sealable opening, for example an opening across which extends an elastomeric membrane, for injection of an antibiotics solution intended for prevention of or for combatting infection.

I claim:

1. A device for implantation in osseous tissue, said device including rotationally symmetric holding means constructed of a tissue compatible material, the holding means having an insertion end and an application end and being provided with an external thread or threads extending from said insertion end thereof towards said application end, holding means having at least one axial bore extending from the application end of the holding means to the insertion end of the holding means;

said device also including an electrically insulating element received in said axial bore extending from said application end, and at least one electrical terminal supported in said insulating element and an electrical conductor connected with said electrical terminal and extending externally of said holding means;

said holding means including a first holding portion comprising a first external thread and a first central bore portion, a second holding portion integrally formed with and extending axially from the first holding portion, said second holding portion having a second central bore portion;

said first and second holding portions and the central bore portion, being rotationally symmetrically arranged with respect to a central axis of the holding means and the outer diameter of the second holding portion being at least as large as the outer diameter of the first holding portion, and the diameter of the second central bore portion being larger than the diameter of the first central bore portion;

said second holding portion being provided with locking means for positional fixation of the insulating element, said locking means including a screw thread formed in said second central bore within said second holding portion and an externally screw-threaded locking ring screwed into the second central bore portion, and bearing upon said insulating element.

2. A device according to claim 1, wherein said holding means has a peripheral wall and has at least one opening in its peripheral wall communicating with said axial bore.

3. A device according to claim 1, in which the electrical conductor connected with said electrical terminal extends through the end of said axial bore at the insertion end of said holding means.

4. A device according to claim 1, also including a connector means insertable in said bore, said connector means including terminal means complementary with said terminal supported in said insulating element.

5. The device of claim 1 in which there is at least one slit that extends from the insertion end of the holding means toward the application end, and said at least one slit being defined by cutting edges which render the holding means self-tapping.

6. A device according to claim 5, wherein at said application end of the holding means there is provided locking means securing said electrically insulating element in position in the holding means.

7. A device according to claim 1, including an electrically insulating element received in the second central bore portion, at least one electrical terminal supported in said insulating element and an electrical conductor connected with said electrical terminal and extending through said first central bore portion.

8. The device of claim 1, in which the second holding portion is provided with a second external thread having the same pitch as the first external thread.

9. The device of claim 1, in which at least said externally screw-threaded portion of the holding means is of titanium or another tissue compatible material and has a micropitted surface with a pit diameter of between 10– 1,000 nm.

10. The device of claim 9, wherein said pit diameter is between 10 and 300 nm.

11. A device for implantation in osseous tissue, said device including rotationally symmetric holding means constructed of a tissue compatible material, the holding means having an insertion end and an application end and being provided with an external thread or threads extending from said insertion end thereof towards said application end, holding means having at least one axial bore extending from the application end of the holding means to the insertion end of the holding means;

said device also including an electrically insulating element received in said axial bore extending from said application end, and at least one electrical terminal supported in said insulating element and an electrical conductor connected with said electrical terminal and extending externally of said holding means;

said holding means including a first holding portion comprising a first external thread and a first central bore portion, a second holding portion integrally formed with and extending axially from the first holding portion, said second holding portion having a second central bore portion;

said first and second holding portions and the central bore portion, being rotationally symmetrically arranged with respect to a central axis of the holding means and the outer diameter of the second holding portion being at least as large as the outer diameter of the first holding portion, and the diameter of the second central bore portion being larger than the diameter of the first central bore portion;

said holding means including an integral end portion extending from the end of said second holding portion remote from the first holding portion, said end portion having substantial rotational symmetry about said central axis of the holding means and bounding a third axial pore portion with a diameter greater than the diameter of said second central bore, said end portion having an internal screw thread.

12. The device of claim 11 in which there is at least one slit that extends from the insertion end of the holding means toward the application end, and said at least one slit being defined by cutting edges which render the holding means self-tapping.

13. The device of claim 11, in which the second holding portion is provided with a second external thread having the same pitch as the first external thread.

14. The device of claim 11, in which at least said externally screw-threaded portion of the holding means is of titanium or another tissue compatible material and has a micropitted surface with a pit diameter of between 10–1,000 nm.

15. The device of claim 14, wherein said pit diameter is between 10 and 300 nm.

16. A device according to claim 11, including an electrically insulating element received within said holding means, at least one electrical terminal supported in said insulating element and an electrical conductor connected with said electrical terminal and extending through said first central bore, said electrically insulating element including a portion fitting within said second bore and an adjoining enlarged portion fitting within said third axial bore portion and forming a flange engaging a shoulder extending between said second and third bore portions, the device including an externally screwthreaded retaining ring in screw-threaded engagement with said internally threaded third bore portion, said flange being clamped between said shoulder and said retaining ring.

* * * * *